(12) United States Patent
Takayama et al.

(10) Patent No.: US 8,313,941 B2
(45) Date of Patent: *Nov. 20, 2012

(54) INTEGRATED MICROFLUIDIC CONTROL EMPLOYING PROGRAMMABLE TACTILE ACTUATORS

(75) Inventors: Shuichi Takayama, Ann Arbor, MI (US); Xiaoyue Zhu, Ann Arbor, MI (US); Wei Gu, Ann Arbor, MI (US); Gary Daniel Smith, Ann Arbor, MI (US); Yunseok Heo, Ann Arbor, MI (US); Brenda S. Cho, Ann Arbor, MI (US); Nobuyuki Futai, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 172 days.

This patent is subject to a terminal disclaimer.

(21) Appl. No.: 12/783,650

(22) Filed: May 20, 2010

(65) Prior Publication Data

US 2010/0233799 A1 Sep. 16, 2010

Related U.S. Application Data

(63) Continuation of application No. 10/548,692, filed as application No. PCT/US2004/007246 on Mar. 10, 2004, now Pat. No. 7,745,211.

(60) Provisional application No. 60/453,298, filed on Mar. 10, 2003.

(51) Int. Cl.
 *C12M 1/00* (2006.01)
 *C12M 1/22* (2006.01)
 *C12M 3/00* (2006.01)

(52) U.S. Cl. ............... 435/286.5; 435/305.1; 435/284.1; 435/287.3; 435/287.8; 435/288.2; 435/293.1; 435/305.2; 435/305.3; 435/307.1; 435/288.3; 435/288.5

(58) Field of Classification Search ............... 435/284.1, 435/287.3, 287.8, 288.2, 288.3, 288.5, 293.1, 435/305.1, 305.2, 305.3, 307.1, 286.5
See application file for complete search history.

(56) References Cited

U.S. PATENT DOCUMENTS

| 4,152,098 A | 5/1979 | Clark et al. |
| 4,574,000 A | 3/1986 | Hunter |

(Continued)

FOREIGN PATENT DOCUMENTS

JP 01-266373 10/1989

(Continued)

OTHER PUBLICATIONS

English Translation of Abstract; Japanese Publication No. 01-266373; Applicant: Res Dev Corp of Japan; Published Oct. 24, 1989 Abstract Only (1 pg).

(Continued)

*Primary Examiner* — Nathan Bowers
(74) *Attorney, Agent, or Firm* — Casimir Jones, S.C.

(57) ABSTRACT

Microfluidic devices having active features such as valves, peristaltic pumps, and mixing portions are fabricated to have a thin elastomeric membrane over the active features. The active features are activated by a tactile actuator external to the membrane, for example, a commercial Braille display. The display may be computer controlled, for example by simple text editor software, to activate individual Braille protrusions or a plurality of protrusions to actuate the active portions of the microfluidic device. Integral devices can incorporate the tactile actuators in a single device, but still external to the membrane.

11 Claims, 4 Drawing Sheets

U.S. PATENT DOCUMENTS

| | | | |
|---|---|---|---|
| 5,153,136 A * | 10/1992 | Vandenburgh | 435/286.1 |
| 5,332,370 A | 7/1994 | Nakayama et al. | |
| 5,496,174 A | 3/1996 | Garner | |
| 5,580,251 A | 12/1996 | Gilkes et al. | |
| 5,685,721 A | 11/1997 | Decker | |
| 5,718,588 A | 2/1998 | Tretiakoff et al. | |
| 5,766,013 A | 6/1998 | Vuyk | |
| 5,842,867 A | 12/1998 | Hong et al. | |
| 6,193,647 B1 | 2/2001 | Beebe et al. | |
| 6,354,839 B1 | 3/2002 | Schmidt et al. | |
| 6,448,069 B1 | 9/2002 | Cecchi et al. | |
| 6,673,008 B1 | 1/2004 | Thompson et al. | |
| 6,695,765 B1 | 2/2004 | Beebe et al. | |
| 6,807,892 B2 | 10/2004 | Biegelsen et al. | |
| 2001/0054778 A1 | 12/2001 | Chou et al. | |
| 2002/0068358 A1 | 6/2002 | Campbell et al. | |
| 2005/0153276 A1 | 7/2005 | Wikswo et al. | |

FOREIGN PATENT DOCUMENTS

| | | |
|---|---|---|
| JP | 08-114409 | 5/1996 |
| JP | 2000-274375 | 10/2000 |
| WO | WO 01/01025 A2 | 1/2001 |
| WO | WO 03/008102 A1 | 1/2003 |
| WO | WO 03/008937 A2 | 1/2003 |

OTHER PUBLICATIONS

English Translation of Abstract; Japanese Publication No. 08-114408; Applicant: Omron Corp; Published May 7, 1996 Abstract Only (1 pg).

English Translation of Abstract; Japanese Publication No. 2000-274375; Applicant: Seiko Epson Corp; Published Oct. 3, 2000 Abstract Only (1 pg).

M.A. Unger et al., Science 2000, 288, p. 113.

Stroock et al., "Chaotic Mixer for Microchannels", Science, Jan. 2002, vol. 295, pp. 647, 651.

Thorsen et al., Microfluidic Large-Scale Integration, Science, Oct. 2002, vol. 298, pp. 580-584.

Robin H. Liu et al., MEMS, Jun. 2000, vol. 9, pp. 190-197, "Passive Mixing in a Three-Dimensional Serpentine Microchannel".

D.C. Duffy et al., "Rapid Prototyping of Microfluidic Systems in Poly(dimethylsiloxane)", Analytical Chemistry 70, 4974-4984 (1998).

J.R. Anderson et al., "Fabrication of Topologically Complex three-Dimensional Microfluidic Systems in PDMS by Rapid Prototyping", Analytical Chemistry, 72, 3158-64 (2000).

* cited by examiner

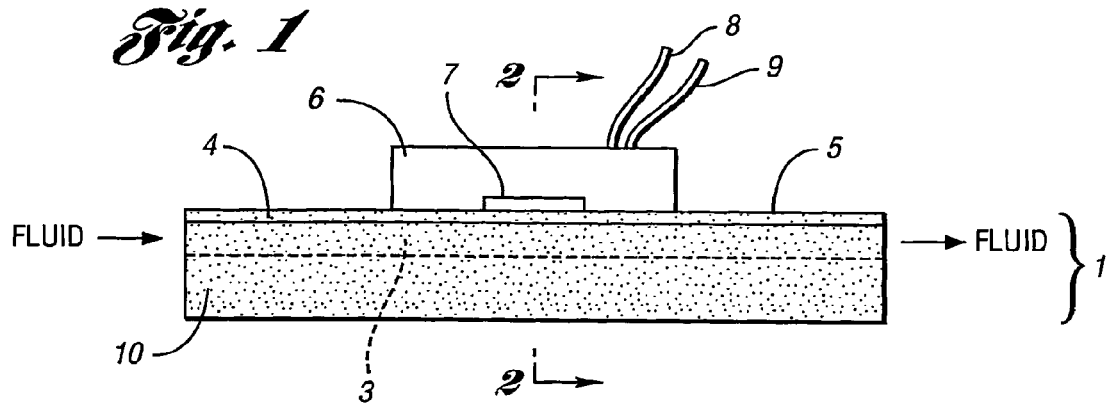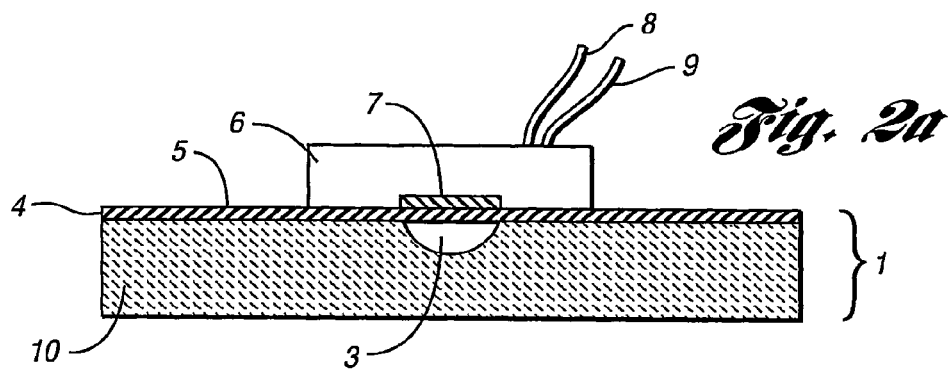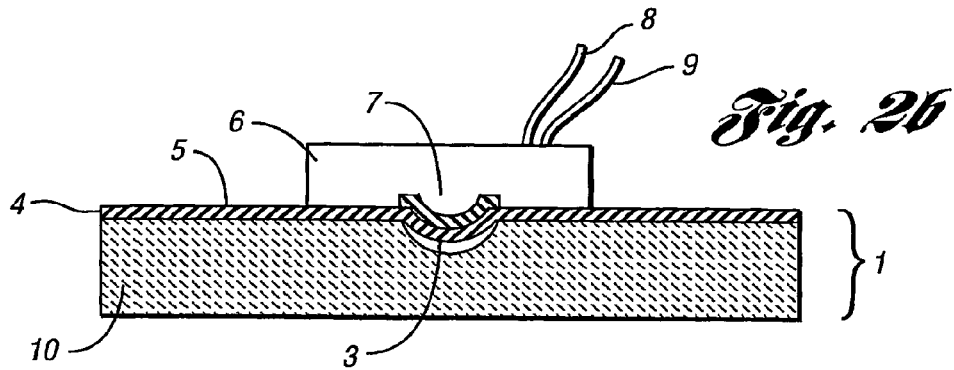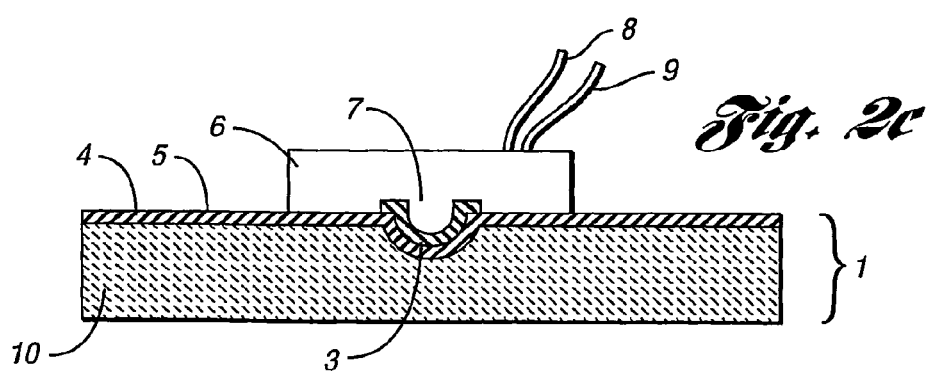

INTEGRATED MICROFLUIDIC CONTROL EMPLOYING PROGRAMMABLE TACTILE ACTUATORS

CROSS REFERFERENCE TO RELATED APPLICATIONS

This application is a continuation of U.S. patent application Ser. No. 10/548,692, Filed: Sep. 8, 2005, now U.S. Pat. No. 7,745,211, which is a U.S. 371 National State Entry of PCT International Patent Application Serial No.: PCT/US2004/007246, Filed: Mar. 10, 2004, which claims priority to U.S. Provisional Patent Application Ser. No.: 60/453,298, Filed: Mar. 10, 2003, each of which are hereby incorporated by reference in their entireties.

BACKGROUND OF THE INVENTION

1. Field of the Invention

The present invention is directed to active microfluidic devices.

2. Background Art

Microfluidic devices are miniature devices generally containing a plurality of interconnected microchannels, reservoirs, etc., of very small size. Microchannels may commonly have width and height dimensions of 10 µm to 300 µm, for example, although smaller and larger dimensions are possible as well. As an aim to miniaturization and cost reduction, it is desirable to construct "lab on a chip" devices which contain all necessary functions with the exception of external fluid supply, and electrical, magnetic, or pneumatic energy supply when appropriate.

Examples of microfluidic devices include micro flow cytometers as disclosed in K. Kurabayashi, et al., "Flow Cytometers and Detection System of Lesser Size," published PCT Application No. WO 03/008937 A2 and motile sperm sorters as disclosed in S. Takayama, et al., "Process for Sorting Motile Particles from Lesser-Motile Particles and Apparatus Suitable Therefor," filed Feb. 27, 2003 under Ser. No. 10/375,373, in the United States Patent and Trademark Office. However, numerous other microfluidic devices are disclosed in the literature, and increasing numbers of different applications are proposed, including chemical microreactors, micro carburetors, micro spectrophotometers, and devices for cell sorting, cell growth, etc. A novel, constant flow gravity driven pumping system is disclosed in S. Takayama et al., "Microfluidic Gravity Flow Pump with Constant Flow Rate," published PCT Application No. WO 03/008102 A1, filed Jul. 18, 2002 under Ser. No. 10/198,477, in the United States Patent and Trademark Office.

In simple devices, flow of gas or liquid through the various flow channels may be initiated and controlled by external devices such as syringes, pipets, micropumps, etc. However, increasing complexity of such devices, the need to pump fluids "on chip," the need to stop, start, or regulate flow, and the need to vary interchannel connectivity has created the desire to incorporate active devices "on chip." Unfortunately, prior attempts to incorporate active valves and pumps have created enormous difficulties with respect to device fabrication, and have often required that the active devices be connected with macroscopic energizing auxiliaries such as pneumatic supply tubing, etc.

For example, the Quake group has disclosed integrated microfluidic systems such as cell sorters with an array of over 2000 individually addressable fluid reservoirs. However, while the number of channels is not limited, the number of individually actuated components is limited due to the need to connect each pneumatic control channel to macroscopic air supply tubes. To compensate, a complex cluster activation scheme has been proposed. However, this scheme is incapable of individually addressing control sites. Moreover, such devices are difficult to fabricate. See, e.g., SCIENCE, January 2002, 295, pp. 647-651, Thorsen et al, Microfluidic Large-Scale Integration, SCIENCE, October 2002, 298, pp. 580-584, and MEMS, June 2000, 9, pp. 190-197. These devices are complex and costly to fabricate.

Peristaltic pneumatic pumps have been disclosed by M. A. Unger et al., SCIENCE 2000, 288, p. 113, in which successive pneumatic passageways cross a microchannel at right angles, and pump fluid through the microchannel by successive application. Once again, a macroscopic energy supply is required, and the device quickly becomes complex when multiple pumps and/or multiple channels are required.

It is well known that certain types of cell cultures, embryo growth, etc. require a changing environment. This changing environment mimics in vivo culture, and may include changing the concentrations of nutrients, growth factors, vitamins, etc., changing pH, presence or absence of growth inhibitors, etc. The changing environment may also be a change in flow rate of fluid or a periodic fluctuation of fluid flow. Changing such factors is typically quite complex.

SUMMARY OF THE INVENTION

The present invention employs an electronically activated and addressable tactile display to serve as active component actuators on microfluidic devices. The tactile display may advantageously be external to the microfluidics device such that macroscopic connectors are not required. Valving, pumping, mixing, cell crushing, and other functions are easily accomplished at low cost, including multiple valves, and pumps and mixers.

BRIEF DESCRIPTION OF THE DRAWINGS

FIG. 1 illustrates one embodiment of the present invention employing an external, non-integral tactile actuator;

FIGS. 2a through 2c illustrate the action of the device of FIG. 1;

DETAILED DESCRIPTION OF THE PREFERRED EMBODIMENT(S)

Figure 3:
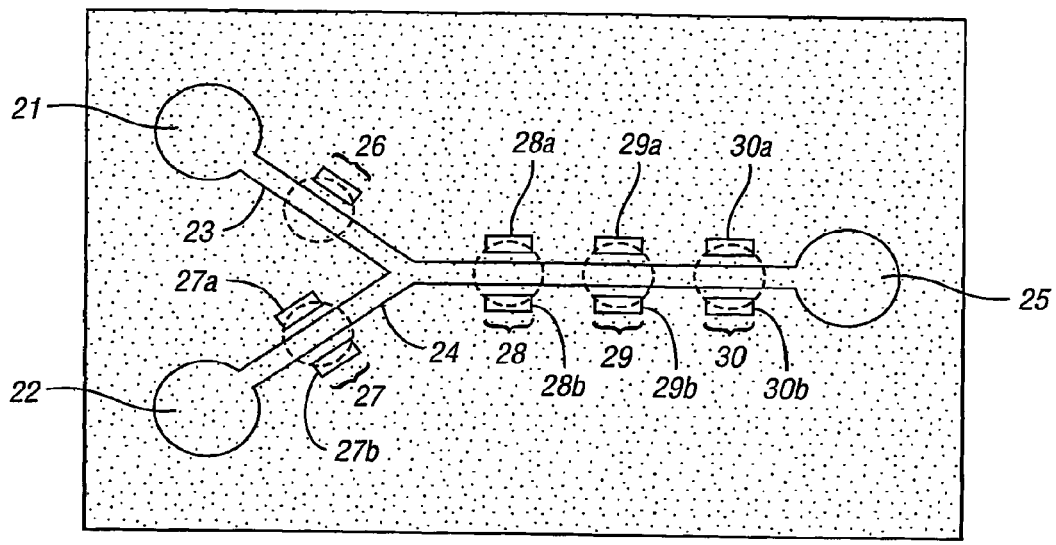
FIG. 3 illustrates a microfluidic device employing tactile actuators to select or control inlet flow and to pump or mix fluid.

The microfluidic devices of the present invention contain microchannels whose flow characteristics are to be actively varied, formed in a compressible or distortable elastomeric material. Thus, it is preferred that substantially the entire microfluidic device be constructed of a flexible elastomeric material such as an organopolysiloxane elastomer ("PDMS"), as described hereinafter. However, the device substrate may also be constructed of hard, i.e., substantially non-elastic material at portions where active control is not desired, although such construction generally involves added construction complexity and expense. The generally planar devices preferably contain a rigid support of glass, silica, rigid plastic, metal, etc. on one side of the device to provide adequate support, although in some devices, actuation from both major surfaces may require that these supports be absent, or be positioned remote to the elastomeric device itself.

The microfluidic devices of the present invention contain at least one active portion which alters the shape and/or volume of chambers or passageways ("empty space"), particularly fluid flow capabilities of the device. Such active portions include, without limitation, mixing portions, pumping portions, valving portions, flow portions, channel or reservoir selection portions, cell crushing portions, unclogging portions, etc. These active portions all induce some change in the fluid flow, fluid characteristics, channel or reservoir characteristics, etc. by exerting a pressure on the relevant portions of the device, and thus altering the shape and/or volume of the empty space which constitutes these features. The term "empty space" refers to the absence of substrate material. In use, the empty space is usually filled with fluids, microorganisms, etc.

The active portions of the device are activatable by pressure to close their respective channels or to restrict the cross-sectional area of the channels to accomplish the desired active control. To achieve this purpose, the channels, reservoirs, etc. are constructed in such a way that modest pressure from the exterior of the microfluidic device causes the channels, reservoirs, etc. ("microfluidic features") to compress, causing local restriction or total closure of the respective feature. To accomplish this result, the walls within the plane of the device surrounding the feature are preferably elastomeric, and the external surfaces (e.g., in a planar device, an outside major surface) are necessarily elastomeric, such that a minor amount of pressure causes the external surface and optionally the internal feature walls to distort, either reducing cross-sectional area at this point or completely closing the feature.

The pressure required to "activate" the active portion(s) of the device is supplied by an external tactile device such as are used in refreshable Braille displays. The tactile actuator contacts the active portion of the device, and when energized, extends and presses upon the deformable elastomer, restricting or closing the feature in the active portion. This action may be illustrated by reference to FIGS. 1, 2a, 2b, and 2c.

FIG. 1 illustrates a microfluidic device 1 having a channel 2 in a substrate 10 of elastomeric material, on top of which is an elastomeric cover 4. Contacting the top surface 5 of the cover is tactile device 6, having a tactile actuator 7 extendable downwardly by application of an actutating signal through wires 8, 9. In FIG. 2a, the device of FIG. 1 is illustrated in cross-section across 2-2, i.e., in a plane containing the tactile actuator. The channel 3 in FIG. 2a is shown unobstructed, i.e., the tactile activator has not been energized.

In FIG. 2b, an enlarged view across 2-2 of FIG. 1, the tactile activator has been partially energized, with the result that it protrudes away from the tactile device 6, exerting pressure on top surface 5 of the device, and distorting the cover 4 and the walls 11 of the channel 3. As a result, the channel cross-section is decreased, and flow restricted accordingly. A portion of channel 3 has been closed off by the bulge 12 of the energized tactile activator. In such devices, the elastomer material surrounding the feature, here the channel 3, may be, if desired, restricted to the elastomeric cover 4. In other words, the walls of the channel which are within the substrate 10 may be rigid, i.e., of micromachined silica, silicon, glass, hard plastic, metal, etc. The flexible elastomeric portion is restricted in this embodiment to the cover.

In FIG. 2c, the actuator is further ("fully") energized, as a result of which the channel 3 is completely obscured. In this case, the tactile actuator serves as an on/off valve rather than an adjustable flow controller.

In the embodiments shown, rather than close or restrict a feature by being energized, the tactile actuator may be manufactured in an extended position, which retracts upon energizing, or may be applied to the microfluidics device in an energized state, closing or restricting the passage, further opening the passage upon de-energizing.

A significant improvement in the performance, not only of the subject invention devices, but of other microfluidic devices which use pressure, i.e., pneumatic pressure, to activate device features, may be achieved by molding the device to include one or more voids adjacent the channel walls. These voids allow for more complete closure or distortion of the respective feature. An example of such construction is shown in FIG. 3. In FIG. 3, the device, shown from above in plan with the elastomeric cover (4 in FIG. 1) removed, a channel 20 is supplied fluid from supply reservoirs 21, 22 through "active" supply channels 23, 24. Fluid from the channel 20 exits into outlet reservoir 25. Five active portions are shown in the device at 26, 27, 28, 29, and 30. In active portions 27 through 30, the respective channels (24, 20) are flanked by voids 27a and 27b, 28a and 28b, 29a and 29b, and 30a and 30b. Active portion 26 is flanked by but one void, 26a. The dotted circles in the active portions indicate where the tactile actuator will be energized to restrict or close the channel at these points.

Figure 4:
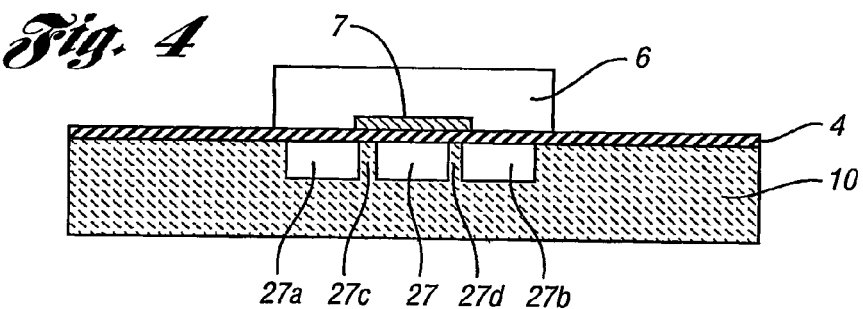
FIG. 4 illustrates a microfluidic channel having flanking voids to facilitate restriction of the channel by a tactile actuator.

In FIG. 4, the channel 24 and active portion 27 are shown in a plane orthogonal to the channel length, in this case with cover 4 and tactile device 6 and tactile activator 7 in place. When the actuator 7 bulges downwards, the walls 27c, 27d between channel 27 and its flanking voids 27a and 27b may distort, allowing for increased flexure at these active portions.

FIG. 3 also illustrates a peristaltic pump made possible by use of three active portions in series, i.e., active portions 28, 29, and 30. By successively actutating end to end, pumping action may be obtained in either direction. By cycling the pumping action back and forth, or by energizing the active portions in an alternative pattern, a mixing action rather than a pumping action may be maintained.

The preferred actuators at the present time are programmable Braille display devices such as those previously commercially available from Telesensory as the Navigator™ Braille Display with Gateway™ software which directly translates screen text into Braille code. These devices generally consist of a linear array of "8-dot" cells, each cell and each cell "dot" of which is individually programmable. Such devices are used by the visually impaired to convert a row of text to Braille symbols, one row at a time, for example to "read" a textual message, book, etc. These devices are presently preferred because of their ready commercial availability. The microfluidic device active portions are designed such that they will be positionable below respective actutable "dots" or protrusions on the Braille display. Braille displays are available from Handy Tech, Blazie, and Alva, among other suppliers.

However, to increase flexibility, it is possible to provide a regular rectangular array usable with a plurality of microfluidics devices, for example having a 10×10, 16×16, 20×100, 100×100 or other array. The more close the spacing and the higher the number of programmable extendable protrusions, the greater is the flexibility in design of microdevices. Production of such devices follows the methods of construction known in the art. Addressability also follows from customary methods. Non-regular arrays, i.e. in patterns having actuators only where desired are also possible. Actuating pins may be used as described in U.S. Pat. No. 5,842,867, herein incorporated by reference.

Devices can also be constructed which integrate the tactile actuators with the microfluidics device. The actuators are still located external to the microfluidics device itself, but attached or bonded thereto to form an integrated whole. For example, U.S. Pat. No. 5,580,251, herein incorporated by reference, discloses a Braille display device having a plurality of cavities having a positive and a negative electrode, the cavities filled with a polar organic gel maintained in the cavity by a flat elastomeric film. Upon application of a voltage differential between the electrodes, the gel in the cavity expands to raise a dimple in the elastomeric film. Such tactile actuating devices may be constructed of glass having metal plated cylindrical cavities, surmounted by a glass or rigid plastic top sheet which is provided with metal electrodes which will be located at the ends of the cylindrical cavities (but not touching the cylindrical metal plated electrodes). The cavity is filled with a polar organic gel such as a polyacrylamide gel. The elastomeric film which raises protrusions upon activation may be an elastomeric silicone film, and may form the elastomeric film 4 (FIG. 1) of the subject matter microfluidic devices.

A somewhat more complicated tactile actuator device is illustrated by U.S. Pat. No. 5,496,174, herein incorporated by reference, which employs a buildup of an electrorheological fluid. Such devices are more amenable to separate tactile actuating devices rather than integral actuating devices. U.S. Pat. No. 5,718,588 discloses a simple electromechanical Braille-type device employing shape memory wires for displacement between "on" and "off" portions. Any known device or device yet to be developed may be used appropriately, especially those employing electrorheologic or magnetorheologic working fluids or gels. A pneumatically operated Braille device is disclosed in U.S. Pat. No. 6,354,839, herein incorporated by reference. Use of "voice coil" type structures, especially those employing strong permanent magnets are also contemplated. Other devices employing shape memory alloys and intrinsically conducting polymer sheets, are respectively disclosed in U.S. Pat. Nos. 5,685,721 and 5,766, 013, herein incorporated by reference. The skilled electrical engineer can readily fabricate such devices.

Figure 5:
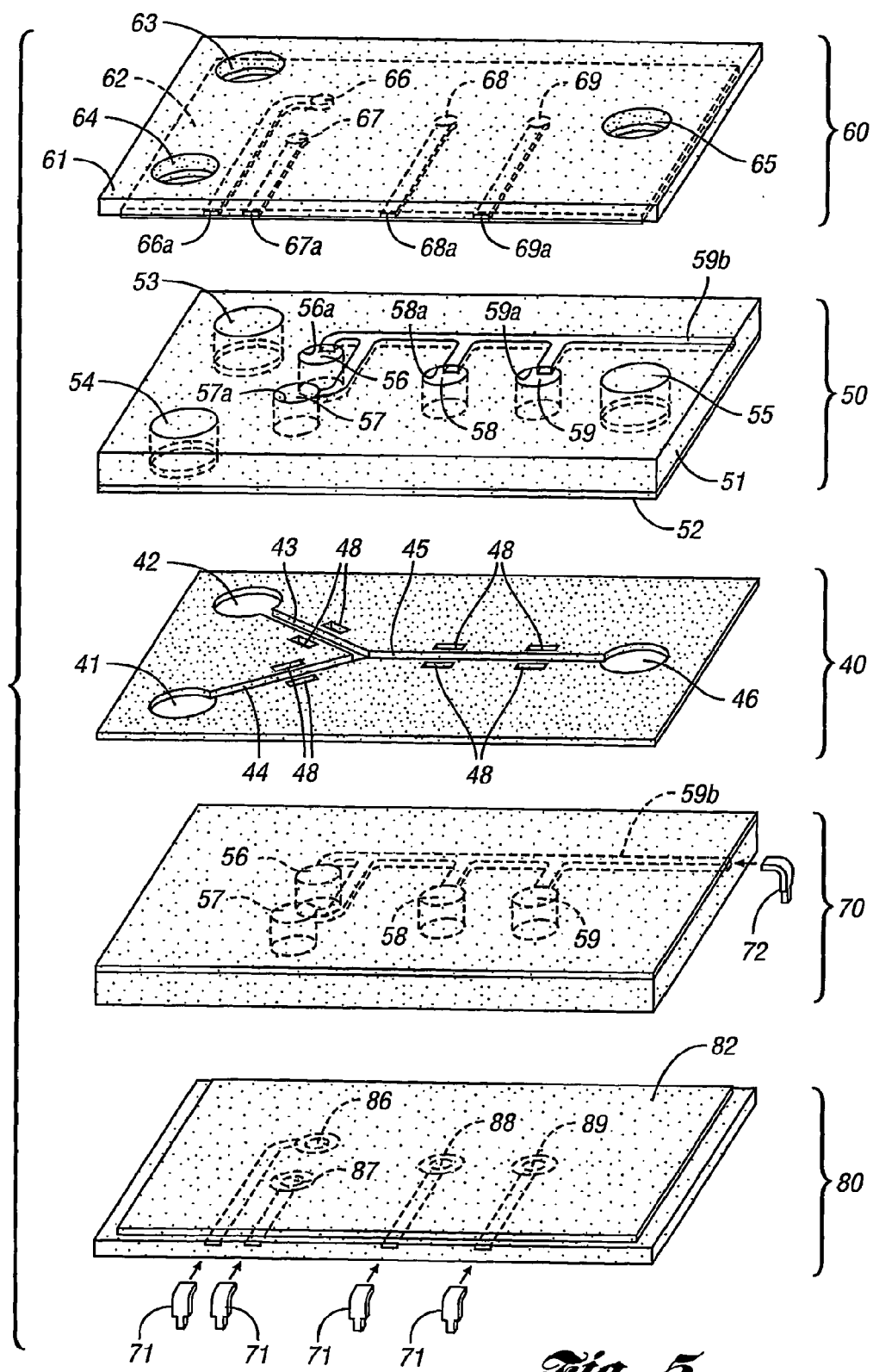
FIG. 5 illustrates an integral device employing two tactile actuator sensor arrays.

An example of a wholly integrated device is illustrated by FIG. 5, consisting of nine layers and five subassemblies. The microfluidic device itself 40 is cast in a single layer of elastomer, in this case of a thickness corresponding to the desired channel height, for example 30 μm. Two inlet reservoirs 41 and 42 feed through inlet channels 43 and 44 to a central channel 45, which terminates at outlet reservoir 46. Four active portions are shown, one on each inlet channel, allowing flow control of each channel 43, 44, including switching between channels, and two further active portions along the central channel 45, which can be alternatively pulsed to mix the fluid stream in the channel, to crush cells in the channel, etc. Each of the active portions of device 40 an be identified by the optional flanking voids 48 in the active portions. The reservoirs, channels, and voids in this embodiment extend through the entire thickness of the device single layer 40. However, devices of multiple layers are also useful.

Positionable atop device 40 is subassembly 50, which consists of a rigid substance, for example a glass, ceramic, or rigid plastic substrate 51, and elastomeric layer 52. Subassembly 50 contains three through holes 53, 54, and 55, which can communicate with reservoirs 42, 41, and 46, respectively, when the layers are combined. Subassembly 50 also contains four cavities or wells, 56, 57, 58, and 59 which extend through substrate 51 but not elastomeric film 52. The inside surfaces 56a through 59a are metal plated to serve as an actuator electrode. These electrodes are commonly connected by metal foil or trace 59b, which serves as a common voltage supply to all cavities. The cavities, prior to final assembly, will be filled with organic polar fluid or gel as previously described.

Subassembly 60 consists of rigid cover 61 and elastomeric insulative seal 62. Both the cover 61 and seal 62 are pierced by through holes 63, 64, and 65, which when assembled, allow communication through corresponding holes 53, 54, 55 in subassembly 50, and ultimately with reservoirs 42, 41, and 46 in the microfluidic device. The combination of these allows for the fluid reservoirs to be filled or emptied, e.g. by a syringe, etc. Extending downward from rigid cover 61 and through seal 62 are electrode buttons 66, 67, 68, and 69, and in electrical communication with these electrodes but between the seal 62 and the rigid cover 61, are conductive traces 66a, 67a, 68a, and 69a.

Subassembly 70 is substantially a mirror image of subassembly 50, but does not contain through holes for communication with the reservoir. The various features are labeled as in subassembly 50. The conductive trace is offset from that of subassembly 50 so that the respective actuators can be independently controlled.

Subassembly 80 is substantially a mirror image of subassembly 60, but again no through holes for reservoir communication are provided. A portion of the total number of dip pin connectors 71, 72 are shown in subassemblies 70, 80. Corresponding connectors are used to connect with the electrical traces of subassemblies 50, 60, but are omitted for clarity. Electrodes 86, 87, 88, and 89 allow for individual actuation of the extendable protrusions.

Figure 6:
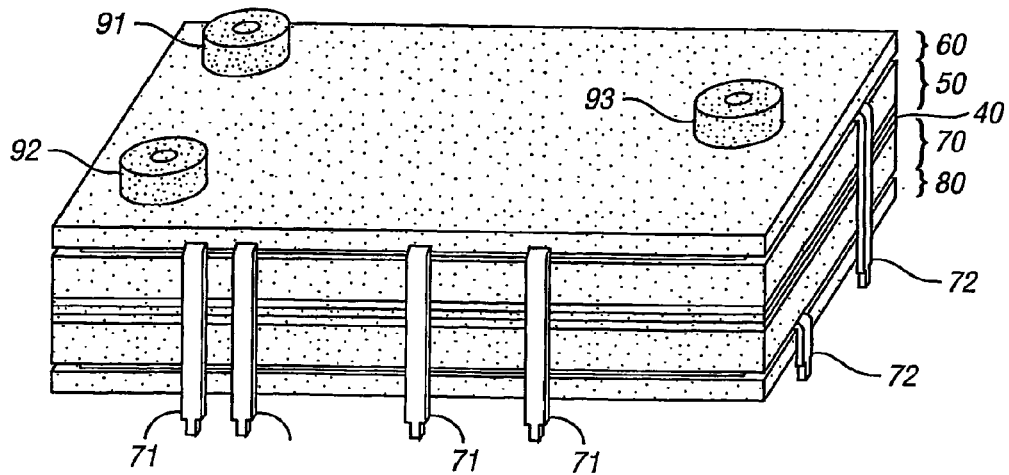
FIG. 6 illustrates an assembled device of FIG. 5.

FIG. 6 illustrates the appearance of a completed device, with fluid connectors 91, 92, 93 attached to the cover 61 to facilitate fluid supply to the reservoir. The dip pin connectors on the back side of the device are not observable in this view. The entire device may be encapsulated with thermosetting resin, as is common for integrated circuits, leaving only fluid connectors 91, 92, 93 and electrical connectors 71, 72 extending out of the integrated device.

The integrated device of FIGS. 5 and 6 may also be created in separate components. In such a case, the actuator assemblies, i.e. subassemblies 50, 60 and 70, 80 may be prepared as separate units. In such a case, the microfluidic device 40 will be surmounted, top and bottom, with an additional elastomeric layer. Use of such non-integral structures allows the actuator portions to be repeatedly reused, replacing only the microfluidic device layers.

Suitable Braille display devices suitable for non-integral use are available from Handy Tech Electronik GmbH, Horb, Germany, as the Graphic Window Professional™ (GWP), having an array of 24×16 tactile pins. Pneumatic displays operated by microvalves have been disclosed by Orbital Research, Inc. said to reduce the cost of Braille tactile cells from 70 $ U.S. per cell to Ca. 5-10 $/cell. Piezoelectric actuators are also usable, for example in devices as shown in FIGS. 5 and 6, where a piezoelectric element replaces the electrorheological fluid, and electrode positioning is altered accordingly.

The microfluidic devices of the present invention have many uses. In cell growth, the nutrients supplied may need to be varied to simulate availability in living systems. By providing several supply channels with active portions to close or restrict the various channels, supply of nutrients and other fluids may be varied at will. An example is a three dimensional scaffolding system to create bony tissue, the scaffolding supplied by various nutrients from reservoirs, coupled with peristaltic pumping to simulate natural circulation.

A further application involves cell crushing. Cells may be crushed by transporting them in channels through active portions and actuating channel closure to crush the cells flowing through the channels. Cell detection may be achieved, for example, by flow cytometry techniques using transparent microfluidic devices and suitable detectors. Embedding optical fibers at various angles to the channel can facilitate detection and activation of the appropriate activators. Similar detection techniques, coupled with the use of valves to vary the delivery from a channel to respective different collection sites or reservoirs can be used to sort embryos and microorganisms, including bacteria, fungi, algae, yeast, viruses, sperm cells, etc.

Growth of embryos generally require a channel or growth chamber which is capable of accommodating the embryo and allowing for its subsequent growth. Such deep channels cannot effectively be closed, however. A microfluidics device capable of embryo growth may be fabricated by multiexposure photolithography, using two masks. First, a large, somewhat rectangular (200 µm width×200 µm depth) channel, optionally with a larger 200 µm deep by 300 µm length and 300 µm width growth chamber at one end is fabricated. Merging with the 200 µm×200 µm channel is a smaller channel with a depth of ca. 30 µm, easily capable of closure by a Braille pin. Exiting the bulbous growth chamber are one or more thin (30 µm) channels. In operation, embryo and media are introduced into the large channel and travel to the bulbous growth chamber. Because the exit channels from the growth chamber are very small, the embryo is trapped in the chamber. The merging channels and exit channels can be used to supply nutrients, etc., in any manner, i.e. continuous, pulsating, reverse flow, etc. The embryo may be studied by spectroscopic and/or microscopic methods, and may be removed by separating the elastomeric layer covering the PDMS body which houses the various channels.

Construction of fluidic devices is preferably performed by soft lithography techniques, as described, for example by D. C. Duffy et al., Rapid Prototyping of Microfluidic Systems in Poly(dimethylsiloxane), ANALYTICAL CHEMISTRY 70, 4974-4984 (1998). See also, J. R. Anderson et al., ANALYTICAL CHEMISTRY 72, 3158-64 (2000); and M. A. Unger et al., SCIENCE 288, 113-16 (2000). Addition-curable RTV-2 silicone elastomers such as SYLGARD® 184, Dow Corning Co., can be used for this purpose.

The dimensions of the various flow channels, reservoirs, growth chambers, etc. are easily determined by volume and flow rate properties, etc. Channels which are designed for complete closure must be of a depth such that the elastomeric layer between the microchannel and the actuator can approach the bottom of the channel. Manufacturing the substrate of elastomeric material facilitates complete closure, in general, as does also a cross-section which is rounded, particularly at the furthest corners (further from the actuator). The depth will also depend, for example, on the extension possible for the actuator's extendable protrusions. Thus, channel depths may vary quite a bit. A depth of less than 100 µm is preferred, more preferably less than 50 µm. Channel depths in the range of 10 µm to 40 µm are preferred for the majority of applications, but even very low channel depths, i.e. 1 nm are feasible, and depths of 500 µm are possible with suitable actuators, particularly if partial closure ("partial valving") is sufficient.

The substrate may be of one layer or a plurality of layers. The individual layers may be prepared by numerous techniques, including laser ablation, plasma etching, wet chemical methods, injection molding, press molding, etc. However, as indicated previously, casting from curable silicone is most preferred, particularly when optical properties are important. Generation of the negative mold can be made by numerous methods, all of which are well known to those skilled in the art. The silicone is then poured onto the mold, degassed if necessary, and allowed to cure. Adherence of multiple layers to each other may be accomplished by conventional techniques.

A preferred method of manufacture of some devices employs preparing a master through use of a negative photoresist. SU-8 50 photoresist from Micro Chem. Corp., Newton, Mass., is preferred. The photoresist may be applied to a glass substrate and exposed from the uncoated side through a suitable mask. Since the depth of cure is dependant on factors such as length of exposure and intensity of the light source, features ranging from very thin up to the depth of the photoresist may be created. The unexposed resist is removed, leaving a raised pattern on the glass substrate. The curable elastomer is cast onto this master and then removed.

The material properties of SU-8 photoresist and the diffuse light from an inexpensive light source can be employed to generate microstructures and channels with cross-sectional profiles that are "rounded and smooth" at the edges yet flat at the top (i.e. bell-shaped). Short exposures tend to produce a radiused top, while longer exposures tend to produce a flat top with rounded corners. Longer exposures also tend to produce wider channels. These profiles are ideal for use as compressive, deformation-based valves that require complete collapse of the channel structure to stop fluid flow, as disclosed by M. A. Unger, et al., SCIENCE 2000, 288, 113. With such channels, Braille-type actuators produced full closure of the microchannels, thus producing a very useful valved microchannel. Such shapes also lend themselves to produce uniform flow fields, and have good optical properties as well.

In a typical procedure, a photoresist layer is exposed from the backside of the substrate through a mask, for example photoplotted film, by diffused light generated with an ultraviolet (UV) transilluminator. Bell-shaped cross-sections are generated due to the way in which the spherical wavefront created by diffused light penetrates into the negative photoresist. The exposure dose dependent change in the SU-8 absorption coefficient (3985 $m^{-1}$ unexposed to 9700 $m^{-1}$ exposed at 365 nm) limits exposure depth at the edges.

The exact cross-sectional shapes and widths of the fabricated structures are determined by a combination of photomask feature size, exposure time/intensity, resist thickness, and distance between the photomask and photoresist. Although backside exposure makes features which are wider than the size defined by the photomask and in some cases smaller in height compared to the thickness of the original photoresist coating, the change in dimensions of the transferred patterns is readily predicted from mask dimensions and exposure time. The relationship between the width of the photomask patterns and the photoresist patterns obtained is essentially linear (slope of 1) beyond a certain photomask aperture size. This linear relationship allows straightforward compensation of the aperture size on the photomask through simple subtraction of a constant value. When exposure time is held constant, there is a threshold aperture size below which incomplete exposure will cause the microchannel height to be lower than the original photoresist thickness. Lower exposure doses will make channels with smoother and more rounded cross-sectional profiles. Light exposure doses that are too slow (or photoresist thicknesses that are too large), however, are insufficient in penetrating through the photoresist, resulting in cross-sections that are thinner than the thickness of the original photoresist.

The suitability of bell-shaped cross-section microchannels of 30 μm thickness to be used as deformation-based valves was evaluated by exerting an external force onto the channel using a piezoelectric vertical actuator of commercially available refreshable Braille displays. Spaces may be left between the membrane and the wall when the channel cross-section has discontinuous tangents, such as in rectangular cross-sections. In contrast, a channel with a bell-shaped cross-section is fully closed under the same conditions. When a Braille pin is pushed against a bell-shaped or rectangular-shaped cross-section microchannel through a 200 μm poly(dimethylsiloxane) (PDMS) membrane, the bell-shaped channels were fully closed while the rectangular channels of the same width had considerable leakage.

The technique described is cost- and time-effective compared to other photolithographic methods for generating well defined rounded profiles such as gray-scale mask lithography, or laser beam polymerization because there is no need for special equipment such as lasers, collimated light sources (mask aligner), or submicron resolution photomasks; it only requires a transilluminator available in many biological labs. In addition, the backside exposure technique can generate more profiles compared to other soft lithography-based patterning methods such as microfluidic mask lithography and the use of patterned laminar flows of etchant in an existing microchannel.

When used as deformation-based microfluidic valves, these bell-shaped microchannels showed improved self-sealing upon compression compared to conventional rectangular or semi-circular cross-section channels as demonstrated by simulations, and by experiments. A bell-shaped channel (width: 30 μm; height 30 μm) was completely closed by an 18 gf-force squeeze of a Braille pin. It is notable that channels that have the bell-shaped cross-sections with "gently sloping" sidewalls cannot be fabricated by melting resist technology, one of the most convenient methods to fabricate photomask-definable rounded patterns, because the profile is determined by surface tension. The bell-shaped channels maximize the cross-sectional area within microfluidic channels without compromising the ability to completely close channels upon deformation. For example, the channel cross-section described here is larger than previously reported, pneumatically actuated deformation-based valves (100 μm in width; 20 μm in height) and may be more suitable for mammalian cell culture. Furthermore, the bell-shaped cross-sections provide channels with flat ceilings and floors, which is advantageous for reducing aberrations in optical microscopy and in obtaining flow fields with a more uniform velocity profile across the widths of the channel. These advantages of microchannels with bell-shaped cross-sectional shapes combined with the convenient, inexpensive, and commercially available valve actuation mechanism based on refreshable Braille displays will be useful for a wide range of microfluidic applications such as microfluidic cell culture and analysis systems, biosensors, and on-chip optical devices such as microlenses.

The extension outwards of the tactile actuators must be sufficient for their desired purpose. Complete closure of a 40 μm deep microchannel, for example, will generally require a 40 μm extension ("protrusion") or more when a single actuator is used, and about 20 μm or more when dual actuators on opposite sides of the channel are used. For peristaltic pumping, mixing, and flow regulation, lesser extensions relative to channel height are useful. The areal size of the tactile activators may vary appropriately with channel width and function (closure, flow regulation, pumping, etc.), and may preferably range from 40 μm to about 2 mm, more preferably 0.5 mm to 1.5 mm. Larger and smaller sizes are possible as well. The actuators must generate sufficient force. The force generated by one Braille-type display pin is approximately 176 mN, and in other displays may be higher or lower.

Thus, in one aspect, the invention pertains to a microfluidic device having at least one active portion consisting of a fluid channel or repository, having an elastomeric cover and optionally but preferably, elastomeric walls, the volume and/or cross-sectional area of which may be selectively varied by imposition of pressure from a tactile actuator external to the microfluidic device. In a further aspect of the invention, an array of tactile actuators may be used to supply the actuating pressure, the individual tactile protrusions being capable of being individually addressed or addressed in groups, for example by simple computer programming, or input of an ASCII character string.

In a yet further aspect of the invention, a series of tactile actuators external to a microfluidic channel are actuated in a pattern to provide a peristaltic pumping action or a mixing action with respect to fluid contained in the channel.

In a still further aspect of the invention, tactile actuators are employed to selectively close or open supply or outlet channels of a microfluidic device, optionally in response to signals generated by passage of fluid or particles in one or more channels of the microfluidic device.

In another aspect of the invention, the tactile actuators are maintained external to the microfluidic device per se but are assembled into an integrated structure containing fluid inlets and outlets and electrical connections for energizing respective tactile actuators.

In a further aspect of the invention, the subject invention devices are employed as microreactors, tissue culture devices, cell culture devices, cell sorting devices, or cell crushing devices.

The use of a standard Braille display with commercially available software is a particularly elegant means of actuating device features such as valve closing, pumping, and mixing. The elastomeric microfluidic device is designed such that the appropriate features are positioned below respective Braille protrusions in an 8-dot Braille cell, or below protrusions located in various cells in the display. A text editor with scrolling capability can scan a single or a plurality of lines of ASCII characters, and transfer appropriate signals to the display. Variable speed scrolling can be used to alter the speed of actuation.

For example, ASCII "a" is represented by the digital code 10000000 while a "coma" is represented by 00000100. Each of these codes will actuate a single protrusion in an 8-dot cell. Braille software is available for use in computers operating in numerous environments. For Windows® operating systems, for example, JAWS 4.0 is available. However, the concept is simple and easily implemented in numerous programming languages such as Fortran, Basic, and Visual Basic.

By use of the present invention, numerous functions can be implemented on a single device. Use of multiple reservoirs for supply of nutrients, growth factors, etc. is possible. The various reservoirs make possible any combination of fluid supply, i.e. from a single reservoir at a time, or from any combination of reservoirs. This is accomplished by establishing fluid communication with a reservoir by means of a valved microchannel, as previously described. By programming the Braille display or actuator array, each individual reservoir may be connected with a growth channel or chamber at will. By also incorporating a plurality of extendable protrusions along a microchannel supply, peristaltic pumping may be performed at a variety of flow rates. Uneven, pulsed flow typical of vertebrate circulatory systems can easily be created. Despite the flexibility which the inventive system offers, construction is straightforward. The simplicity of the microfluidics device per se, coupled with a simple, programmable external actuator, enables a cost-effective system to be prepared, where the microfluidic device is relatively inexpensive and disposable, despite its technological capabilities.

Combinatorial, regulated flow with multiple pumps and valves that offer more flexibility in microfluidic cell studies in a laptop to handheld-sized system are created by using a grid of tiny actuators on refreshable Braille displays. These displays are typically used by the visually impaired as tactile analogs to computer monitors. Displays usually contain 20-80 rows of cells, each holding 8 (4×2) vertically moving pins (1-1.3 mm). Two pins on the same cell may typically be 2.45 mm apart center to center and 3.8 mm apart on different cells. Each pin may have the potential to protrude 0.7~1 mm upward using piezoelectric mechanisms, and may hold up to ~15-20 cN. Control of Braille pins actuators is accomplished by changing a line of text in a computer program. Unique combinations of Braille pins will protrude depending on the letters displayed at a given time. Braille displays are prepackaged with software, easy to use, and readily accessible. They are designed for individual use, and range from walkman to laptop sizes while using AC or battery power. By using the moving Braille pins against channels in elastomeric, transparent rubber, it is possible to deform channels and create in situ pumps and valves.

EXAMPLE 1

A microfluidic device is fabricated of PDMS (SYL-GARD® 184) with active portions located below a commercial Braille display having 8-dot cells, the protrusions of which are approximately 1 mm in diameter, at spacings of 2.5 mm center-to-center in each cell, with an intercell distance of 3.2 mm. Each protrusion can protrude 1.5 mm from the surface of the display when activated. The elastomeric PDMS device channels have a relatively thin 100-200 μm bottom PDMS membrane, which rests upon the Braille display. The microfluidic device has a common observation channel and two valved supply channels, and is used to study Braille display actuated valving. The valves are constructed as described earlier with voids adjacent the active portions, and located on the microfluidic device so as to be below dimples on a commercial Braille display. One inlet channel is supplied with a solution of fluorescent dye from an inlet reservoir, while the other inlet reservoir contains no dye. The respective valves are opened and closed repeatedly by scrolling through text containing alternate "a" and ",". The fluorescence in the common channel is monitored. Fluid flow is induced by a syringe communicating with the common channel outlet. The device is thus similar to that of FIG. 3.

Figure 7:
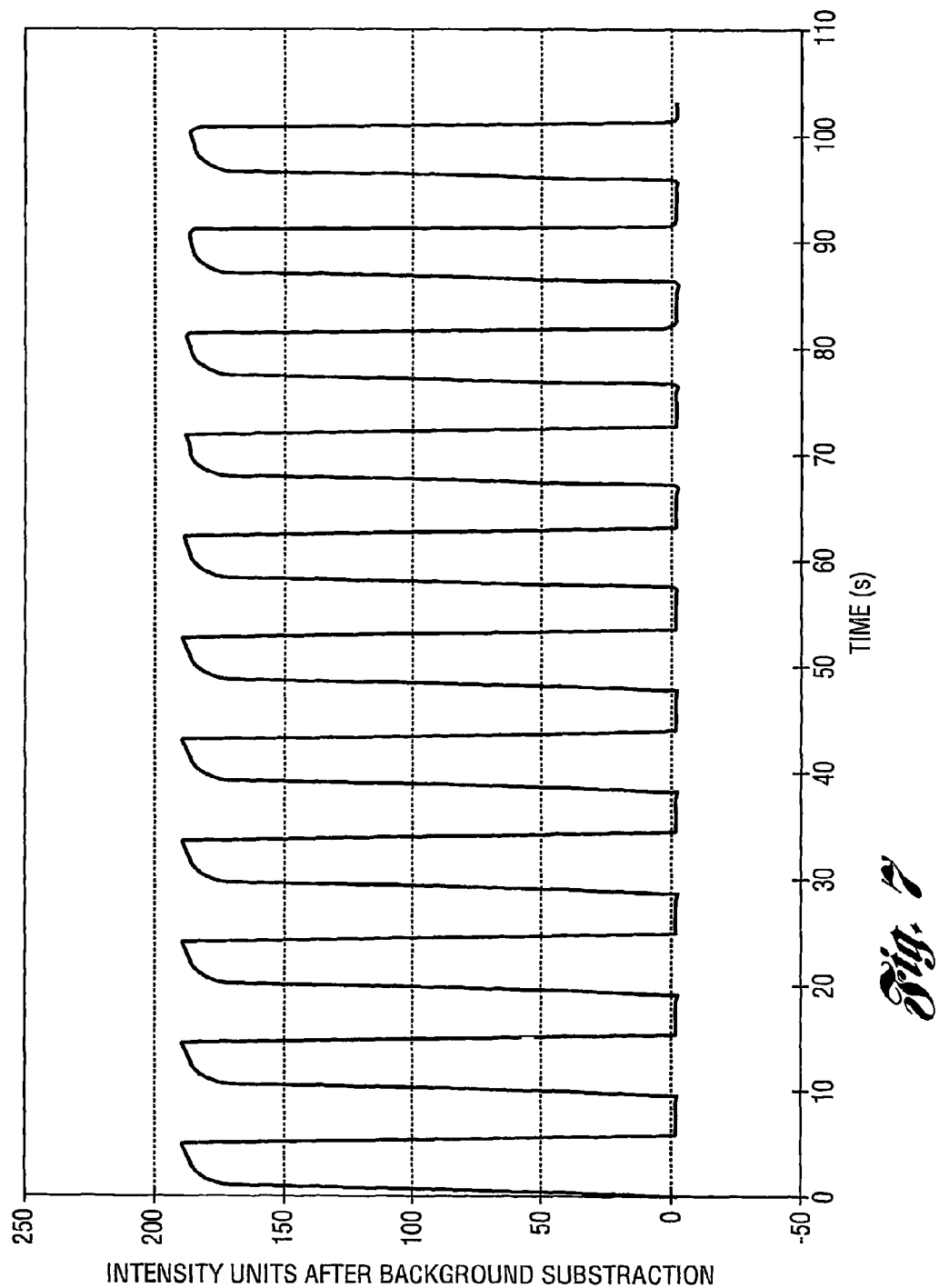
FIG. 7 illustrates valving action in a non-integral device produced by scrolling text onto a Braille display device.

FIG. 7 illustrates the observed fluorescence in the channel as the respective inlet valves were alternately closed, after subtracting background noise. As can be seen, the valving is highly effective. The plot is similar to that presented in M. A. Unger et al., SCIENCE 288, 113 (2000).

EXAMPLE 2

Photoplotted films were ordered from CAD/Art Services, Inc. (Poway, Calif.). Four-inch double-sided polished borosilicate glass wafers (thickness=200 μm) were from Plan Optik GmbH (Elsoff, Germany), 48 mm×65 mm borosilicate cover glasses (thickness=160 μm) from Fisher Scientific, negative photoresist SU-8 50 from MicroChem Corp. (Newton, Mass.), and PDMS (Sylgard 184) from Dow Corning (Midland, Mich.). Photoresist was exposed by a transilluminator (FB-TIV-816A, Fisher Scientific) with six replaced fluorescent blacklight lamps (TL-D15W/08, Philips), and a PLA-501FA mask aligner by Canon U.S.A., Inc. (Lake Success, N.Y.). Oxidation was performed using a plasma etcher (Plasma Prep II; Structure Probe Inc., West Chester, Pa.). A Braille display DotView DV-1 was obtained from KGS Corp. (Saitama, Japan). Phosphate-buffered saline (PBS) was obtained from Fisher Scientific.

Photomasks of microchannels (width: 10 μm~400 μm) were produced by photoplotting at 20,000 dpi to form an exposure mask. A 30 μm layer of SU-8 50 was coated on a glass substrate by spin coating at 4,500 rpm, softbaking at 95 C, and exposing from the backside using a transilluminator at the maximum intensity (8 mW/cm$^2$). A photomask film is placed on the non-coated side of the substrate and sandwiched by two 5-inch composite quartz glass photomask blanks (thickness, 2.38 mm). The coated side of the substrate is covered with a yellow-tinted vinyl film to prevent ultraviolet light from reentering into the SU-8 coating. These were placed on a mobile carriage atop the transilluminator. The gap between the surface of the transilluminator and the substrate was 19 mm. The carriage moves back-and-force in a radial direction at a speed of 5 cm/s. Channel features were obtained after post exposure bake at 95° C., followed by development.

The pattern of the mold was transferred into a 5 mm thick poly(dimethylsiloxane) (PDMS) slab by casting of silicone prepolymer. In addition, a 200 μm thick PDMS membrane was also fabricated by spin coating of prepolymer onto a silanized glass wafer. Both the slab and the membrane were cured on a leveled surface at room temperature for 1 day followed by curing at 60 C for 1 h. The slab was finally cured at 150 C for 15 min. Both the slab and membrane were bonded after oxidation by the methods disclosed by Duffy, ANALYTICAL CHEMISTRY 70, op. cit.

The fabricated PDMS microfluidic device was mechanically fixed to the surface of the Braille display. To observe leakage of the channel, the centerline of the channel was aligned with the center of the Braille pin under a fluorescent stereomicroscope. The Braille pin was then controlled to push the channel upward. The maximum force is 176.4 mN. Channel closure (valving) was analyzed using visualization of fluorescence of the Braille pin through a channel filled with a dye solution. Measurement of electrical resistance of liquid in the channel may also be used, by fixing the tips of two platinum wires (254 μm in diameter) at the ends of a channel containing a conductive solution. As the restriction of the passage increases, the measured resistance increases as well. The inside of the microchannel was filled with green food color.

EXAMPLE 3

Each silicone chip is a multilayer assembly of poly(dimethylsiloxane) (PDMS). The bottom layer is formed at a thickness of 120 μm by spin coating a 1:10 (curing agent: base) ratio of prepolymer (Sylgard 184, Dow-Corning) onto a silanized glass wafer at 200 rpm for 4 minutes. A Si master with positive relief structure is made of photoresist (SU-8, MicroChem) defined through backside diffused-light photolithography as described in Example 2. Prepolymer (1:10 ratio) is cast against the positive relief features to form a ~1 mm middle layer. The resultant negative replica formed channels when sealed by the bottom layer. Holes are punched by sharpened 14-gauge blunt needles through the middle layer towards the top layer. Prepolymer of ratios 1:10 and then 1:20 is successively poured on machined brass molds so that the ceiling of the top layer was richer in prepolymer base, providing a better sealant for future injections by needles. All three cured layers attached firmly together after 30 seconds of exposure to oxygen plasma. This assembly was incubated at 60° C. for 10 minutes. Assembled devices were filled with aqueous fluids (e.g. cell culture media) to preserve the hydrophilic surface properties of the channels, and incubated in 37° incubators overnight.

EXAMPLE 4

The microfluidics device includes a reservoir layer on top of the microfluidic assembly to avoid additional tubing. The reservoir and channels remain a closed system (with the exception of gases) for protection against spills and contamination in non-sterile environments. Reagent can be added or subtracted from this closed system using 30 gauge needles since PDMS acts as a sealant. Prepared devices are aligned onto Braille pins, clamped down, placed near a dish of distilled water, and covered loosely with saran wrap. The entire setup is placed into a dry incubator with a nearby laptop that controls the fluidic movement inside each device.

The channel architecture consists of multiple loops that are interlinked during seeding, and valved shut from each other during fluidic circulation. Each loop is connected to the main reservoir and contains a segment linked to other loops. Since each loop had its inlet and outlet connected to the same reservoir, hydrostatic pressure between the two ends were the same. While one seeding procedure can prepare every recycle loop, each loop can be separated by valves and run independently of one another. To seed the channel, one needle is inserted into one end of the seeding circuit as a vent, and another on the other end carrying cells. Valves define only one path for injected cells to navigate, and allow stagnant flow for cells to attach. This makes precision seeding more convenient and efficient than previous methods.

This design is used to create a cellular flow assay. Seeded cells are first perfused with media rich in growth factors (15% Fetal Bovine Serum), and then with limiting media (2% Horse Serum). When in limiting media, moderate flow rates cause cell growth while slow flow rates shunt growth and cause cell death. In general, proliferation occurs at the upstream end and not the downstream end, suggesting that concentration gradients are present from one end of the loop to the other. Although this may be an artifact of the pump, this trend is consistent at all flow rates, including the slowest pumps which actuate once every 25 seconds.

This flow assay features the ability to selectively position cells, and to regulate their fluidic environment for extended periods of times. These features make possible the study of cells in simulated in vivo environments. Just as a circulatory system overcomes slow mass transport in multicellular organisms, regulated microcirculation will likewise benefit cells residing in microfluidic channels by actively delivering fresh nutrients, removing cellular waste, or providing for concentration. One can arbitrarily treat cells to differentiate, grow, or undergo apoptosis. Cell to cell chemical signaling can be studied by reconfiguring the fluidic direction. Such cellular assays can be used for toxicology, pharmacology, or as a biosensor.

EXAMPLE 5

The invention is further demonstrated by switching between laminar streams and mixing by programming, and by seeding, compartmentalizing, and sustaining C2C12 mouse myoblasts within microfluidic chips over extended time periods (up to 3 weeks), and assaying myoblast proliferation under different flow patterns.

Braille displays (Navigator, Telesensory, Calif., USA) provided a grid of microactuator pins. These pins reflected text displayed on a computer. The most accessible method of control uses a text editor (Boxer) to auto-scroll through a prearranged text designed to actuate the correct Braille pins. More flexible programs, coded in Visual Basic (Microsoft), continually update a line of character corresponding to desired pin actuation. Braille screen readers (HAL, JAWS) directly controlled pin actuation based on the refreshing line of characters. Eight pins (4×2) represented all possible characters. Characters correspond to 213 unique combinations out of 256 possible ones, or 83% of the possible combinations. All combinations for the top three rows of pins representing each character have a corresponding letter and are under full control.

Mouse C2C12 mesenchymal precursor cells are cultured and harvested by conventional methods. Cells are cultured under 5% $CO_2$ on Petri dishes (Fisher) in Dulbecco's Modified Eagle Medium (DMEM) (Invitrogen) media containing 15% Fetal Bovine Serum, 100 ug/ml streptomycin, 100 ug/ml penicillin. Cells are dissociated from dishes with trypsin/EDTA and washed in PBS (Invitrogen). These cells are injected into capillary channels and maintained under the same media. The microchannels are pretreated with media incubation overnight. Cells are cultured in the devices on Braille displays in 5% $CO_2$ at 37° C.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A microfluidics device, comprising: a substrate having therein at least one empty space whose shape and/or volume is desired to be altered, said empty space defined on one side thereof by a deformable elastomer layer; and a tactile actuator proximate a side of said elastomer layer, said tactile actuator having a plurality of spaced apart individually addressable extendable protrusions, at least one of which, when actuated, bears upon said deformable elastomer layer, deforming said layer, and altering the shape and/or volume of said empty space, wherein at least one empty space comprises at least one fluid pumping portion, said fluid pumping portion comprising a flow channel and said tactile actuator programmed to extend and retract said protrusions independently from each other in a sequence which causes liquid to be pumped through said flow channel, and wherein the width of each addressable extendable protrusions is larger than the width of said flow channel, and wherein said addressable extendable protrusions restrict or close said flow channel when actuated, said flow channel communicating with said reservoir and said empty space, such that fluid flows from said reservoir through said empty space.

2. The device of claim 1, wherein said tactile actuator comprises a programmable Braille display.

3. The device of claim 1 comprising at least one valved microchannel, said microchannel having a depth of from 1 µm to 100 µm, said microchannel defined on one side thereof by an elastomeric layer having a thickness of from 1 µm to 1 mm.

4. The device of claim 1, wherein said substrate is an elastomeric material.

5. The device of claim 1, wherein said substrate and said elastomeric layer both comprise a silicone elastomer.

6. The device of claim 1, wherein said said microchannel has a depth of from 10 µm to 40 µm, and wherein said elastomeric layer has a thickness of from 100 µm to 400 µm.

7. A method of pumping fluids comprising, comprising:
 a) contacting the device of claim 1 with one or more liquids; and
 b) actuating said tactile actuator such that liquids are pumped through said flow chanel.

8. The method of claim 7, wherein each valved microchannel further comprises a peristaltic pump.

9. The method of claim 7, where the flow rate of fluid through said empty space is varied by varying the rate of actuation of sequentially positioned extendable protrusions along a microchannel in fluid communication with said empty space.

10. The method of claim 7, wherein the fluid flowing is altered by closing or opening respective microchannel valves associated with a plurality of fluid supply microchannels.

11. The method of claim 7, wherein said tactile actuator is a Braille display, and said individual protrusions are actuated by supplying an ASCII character to said display.

* * * * *